US011445950B2

(12) United States Patent
Kay et al.

(10) Patent No.: US 11,445,950 B2
(45) Date of Patent: Sep. 20, 2022

(54) ENZYME-DEPENDENT FLUORESCENCE RECOVERY OF NADH AFTER PHOTOBLEACHING TO ASSESS DEHYDROGENASE ACTIVITY OF LIVING TISSUES

(71) Applicant: The George Washington University, Washington, DC (US)

(72) Inventors: Matthew Kay, Kensington, MD (US); Angel Moreno, Silver Spring, MD (US); Rafael Jaimes, Riverdale, MD (US)

(73) Assignee: The George Washington University, Washington, DC (US)

( * ) Notice: Subject to any disclaimer, the term of this patent is extended or adjusted under 35 U.S.C. 154(b) by 854 days.

(21) Appl. No.: 16/285,920

(22) Filed: Feb. 26, 2019

(65) Prior Publication Data

US 2019/0183395 A1 Jun. 20, 2019

Related U.S. Application Data

(63) Continuation of application No. PCT/US2017/049169, filed on Aug. 29, 2017.
(Continued)

(51) Int. Cl.
*A61B 5/1486* (2006.01)
*A61B 5/00* (2006.01)
(Continued)

(52) U.S. Cl.
CPC ............ *A61B 5/1486* (2013.01); *A61B 1/043* (2013.01); *A61B 1/0684* (2013.01); *A61B 5/0075* (2013.01); *A61B 5/0084* (2013.01); *A61B 5/1459* (2013.01); *A61B 5/4866* (2013.01); *A61B 5/6852* (2013.01); *A61F 7/00* (2013.01);
(Continued)

(58) Field of Classification Search
CPC ... A61B 5/1486; A61B 5/0075; A61B 5/0084; A61B 5/1459; A61B 5/4866; A61B 5/6852; A61B 1/043; A61B 1/0684; A61B 2017/00057; A61B 2018/00351; A61F 7/00; A61F 2007/0056; A61F 2007/126; G01J 1/4257; G01J 1/429; G01J 2001/4247; G01J 2001/4252
See application file for complete search history.

(56) References Cited

U.S. PATENT DOCUMENTS

2008/0315119 A1   12/2008  Blackmore et al.
2013/0079645 A1*  3/2013   Amirana ............. A61B 1/0676
                                              600/479
(Continued)

*Primary Examiner* — Peter Luong
(74) *Attorney, Agent, or Firm* — Kory D. Christensen

(57) ABSTRACT

The invention provides for a system for in vivo real time measurement of NADH recovery kinetics, comprising: 1) a specific pulse sequence to non-destructively, yet effectively, photobleach NADH for measurement of NADH recovery kinetics; 2) illumination light parameters to acquire NADH fluorescence before and after photobleaching, without causing fluorescence bleaching artifacts, for measurement of NADH recovery kinetics; and 3) configurations for devices capable of photobleaching NADH by at least 10% within tissues for effective measurement of NADH recovery kinetics in tissues within a living subject or excised tissues and organs.

34 Claims, 9 Drawing Sheets

Related U.S. Application Data

(60) Provisional application No. 62/382,669, filed on Sep. 1, 2016.

(51) Int. Cl.
| | | |
|---|---|---|
| *A61F 7/00* | (2006.01) | |
| *G01J 1/42* | (2006.01) | |
| *A61B 1/04* | (2006.01) | |
| *A61B 1/06* | (2006.01) | |
| *A61B 5/1459* | (2006.01) | |
| *A61B 18/00* | (2006.01) | |
| *A61F 7/12* | (2006.01) | |
| *A61B 17/00* | (2006.01) | |

(52) U.S. Cl.
CPC ............. *G01J 1/429* (2013.01); *G01J 1/4257* (2013.01); *A61B 2017/00057* (2013.01); *A61B 2018/00351* (2013.01); *A61F 2007/0056* (2013.01); *A61F 2007/126* (2013.01); *G01J 2001/4247* (2013.01); *G01J 2001/4252* (2013.01)

(56) References Cited

U.S. PATENT DOCUMENTS

| | | |
|---|---|---|
| 2015/0196202 A1 | 7/2015 | Mercader et al. |
| 2016/0120599 A1 | 5/2016 | Amirana et al. |

\* cited by examiner

ENZYME-DEPENDENT FLUORESCENCE RECOVERY OF NADH AFTER PHOTOBLEACHING TO ASSESS DEHYDROGENASE ACTIVITY OF LIVING TISSUES

CROSS-REFERENCE TO RELATED APPLICATIONS

This application is a continuation of Patent Cooperation Treaty (PCT) App. No. PCT/US2017/049169, filed Aug. 29, 2017, for "ENZYME-DEPENDENT FLUORESCENCE RECOVERY OF NADH AFTER PHOTOBLEACHING TO ASSESS DEHYDROGENASE ACTIVITY OF LIVING TISSUES," which claims the benefit of U.S. Provisional Application No. 62/382,669 filed Sep. 1, 2016. The content of both applications is incorporated herein by reference.

FEDERALLY SPONSORED RESEARCH OR DEVELOPMENT

This work was partially supported by National Institutes of Health Grant No. RO1 HL095828. The U.S. government may have certain rights in the invention.

FIELD OF THE INVENTION

The present invention comprises methods and compositions for measuring dehydrogenase enzyme activity in living tissue using a non-destructive optical system.

BACKGROUND OF THE INVENTION

Energy (ATP) production within tissues that have high metabolic rates, such as the heart and brain, is critically dependent upon the production of NADH by the dehydrogenase enzymes of the tricarboxylic acid (TCA) cycle. The TCA cycle, also known as the Krebs cycle and the citric acid cycle, is a critical component of oxidative phosphorylation and its rate of NADH production modulates the rate of ATP production. Enzyme-dependent fluorescence recovery after photobleaching (ED-FRAP) of NADH has been shown to be an effective approach for measuring the rate of NADH production to assess dehydrogenase enzyme activity in cellular preparations and isolated mitochondria suspensions. The present invention is directed to methods and compositions allowing non-destructive ED-FRAP in situ analysis of NADH production within living tissue in a subject animal or excised organs and tissues.

Using cellular preparations and isolated mitochondria suspensions, Combs and Balaban introduced NADH ED-FRAP as an assessment of dehydrogenase activity by measuring the rate of NADH production after NADH photolysis [Combs and Balaban, Biophys J. 80:2018 (2001), Joubert, et al., Biophys J. 86: 629 (2004)]. This rate was independent of the rate of NADH consumption and was proportional to the activity (concentration) of glutamate dehydrogenase (GDH). In those studies, NADH was photobleached at levels between 7-18% and the rate of NADH production was proportional to the level of photobleaching. During NADH ED-FRAP, $NAD^+$ is produced by the photolysis of NADH with the advantage that NAD molecules are not destroyed and the kinetic properties of the tricarboxylic acid (TCA) cycle are not altered. Furthermore, NADH does not diffuse from adjacent regions, in contrast to standard FRAP techniques [Jonsson, et al., Biophys J. 95: 5334 (2008), Meyvis, et al., Pharm Res. 16: 1153 (1999)] since most of the NADH fluorescence signal is confined to mitochondria [Eng, Lynch, and Balaban, Biophys J. 55: 621 (1989)]. Instead, NADH ED-FRAP is dominated by NADH production by the dehydrogenase enzymes of the TCA cycle, this is especially true for cells and tissue that use oxidative phosphorylation as a primary source of ATP. With these unique advantages, NADH ED-FRAP provides additional insight into myocardial energetics, above that of monitoring unbleached NADH fluorescence, by providing a direct real-time assessment of NADH production from specific tissue locations. To date, no studies have demonstrated how the rate of NADH production could be assessed within the myocardium of perfused hearts using NADH ED-FRAP. The present disclosures represent an important advancement because the conditions necessary to measuring the rate of NADH production in living tissue (such as hearts or other tissues and organs in-vivo; or ex-vivo during the transport and transplantation of tissues and organs such as hearts, kidneys, and livers) define the parameters for applying NADH ED-FRAP methods to living tissue in situ within a subject animal or excised organs and tissues.

The present invention arises in part from the observation that NADH ED-FRAP can be used to measure the rate of NADH production from any specific site in the myocardium of contracting perfused hearts using high-power UV light-emitting diodes (LEDs) and high-speed CCD cameras. The optimal energy delivery of 23.8 mJ of UV light (367.5±5.5 nm) was determined by modulating the light intensity and pulse width while measuring the NADH photobleaching fraction and ensuring adequate recovery of fluorescence under a variety of controlled conditions.

are housed within an intravascular catheter or laparoscope suitable (light gray) for minimally invasive NADH ED-FRAP. Individual conduits for the low power LED or fiber optic end of the low power UV light source, the photodetector, and the high power LED or fiber optic end of the high power UV light source, each terminate at the rounded distal tip (black) and a proximal end where they are coupled to the NADH ED-FRAP control unit. The entire apparatus is approximately about 0.5 to 2 meters in length, or any length typical of intravascular catheter or laparoscopic devices.

Figure 1:
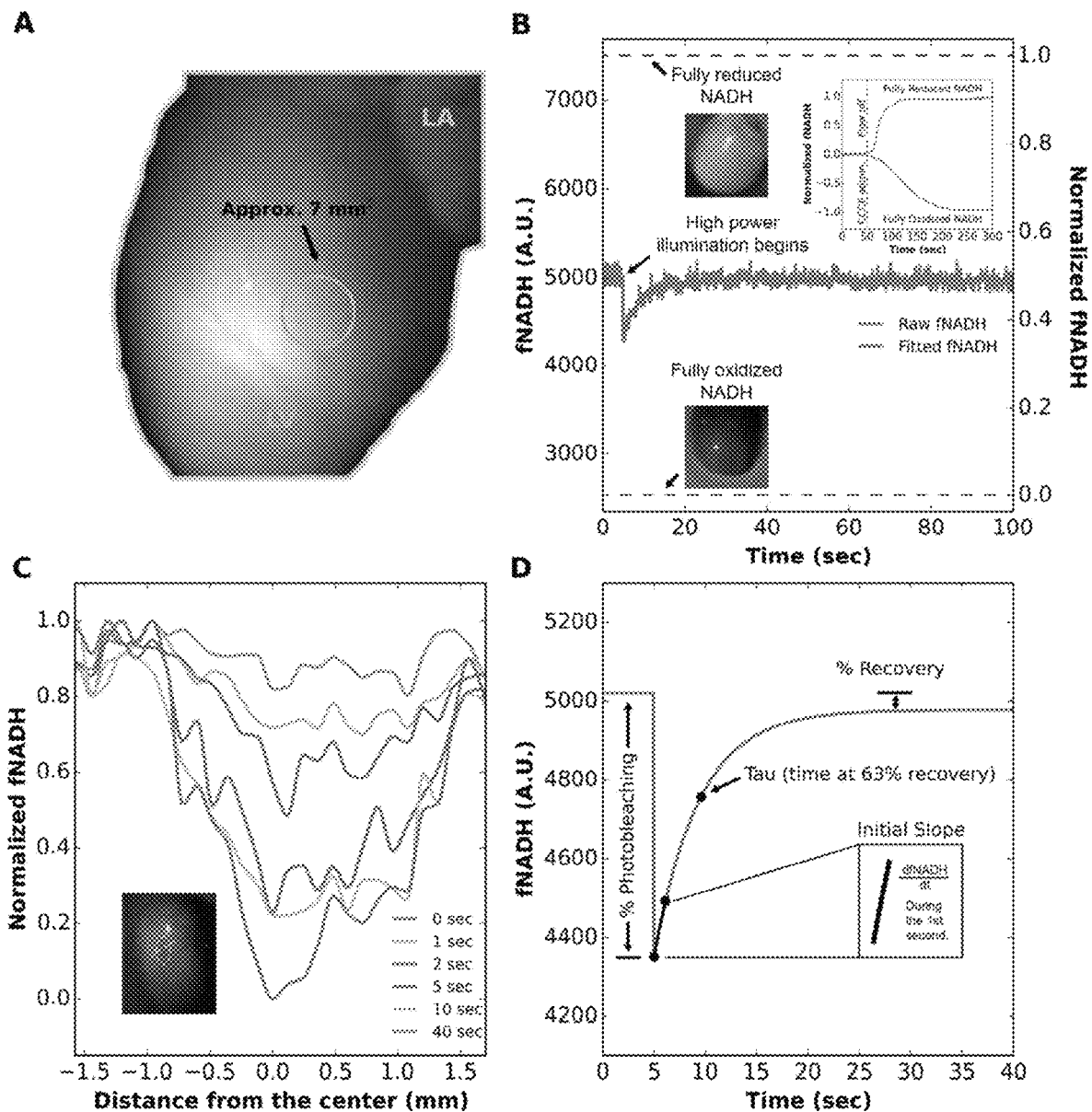
FIG. 1 (Panel A) Photobleaching UV light was focused on the LV epicardium within an area of ~7 $mm^2$ (circle) and delivered as one of four modes described in Table 1. (Panel B) A typical NADH ED-FRAP signal is plotted within the range of the estimated total NADH pool. The application of 23.8 mJ of photobleaching energy typically lowered baseline fNADH by 13.2±2.3%. Inset: Normalized fNADH signals are shown for one heart during full reduction (global ischemia at t=50 sec) and for another heart during full oxidation (CCCP administered at t=50 sec). The non-normalized signals were used to estimate the total NADH pool. (Panel C) An example of spatial fNADH recovery profiles from 0 to 40 sec after photobleaching the area shown in the fNADH image (lighted dotted line). Within 40 sec the spatial fNADH profile returned to baseline levels and was indistinguishable from the fNADH of surrounding unbleached tissue. (Panel D) Measurements extracted from NADH ED-FRAP signals: (1) Percent photobleaching was measured from baseline (fNADH at t<5 sec) to the maximum fNADH drop (fNADH at t=5 sec); (2) Percent recovery was measured from baseline to the steady-state fNADH recovery value; (3) Recovery time constant tau was measured as the time to 63% of full fNADH recovery; (4) The initial slope of recovery was measured as the straight-line slope of change in fNADH during the first second of recovery.
Figure 2:
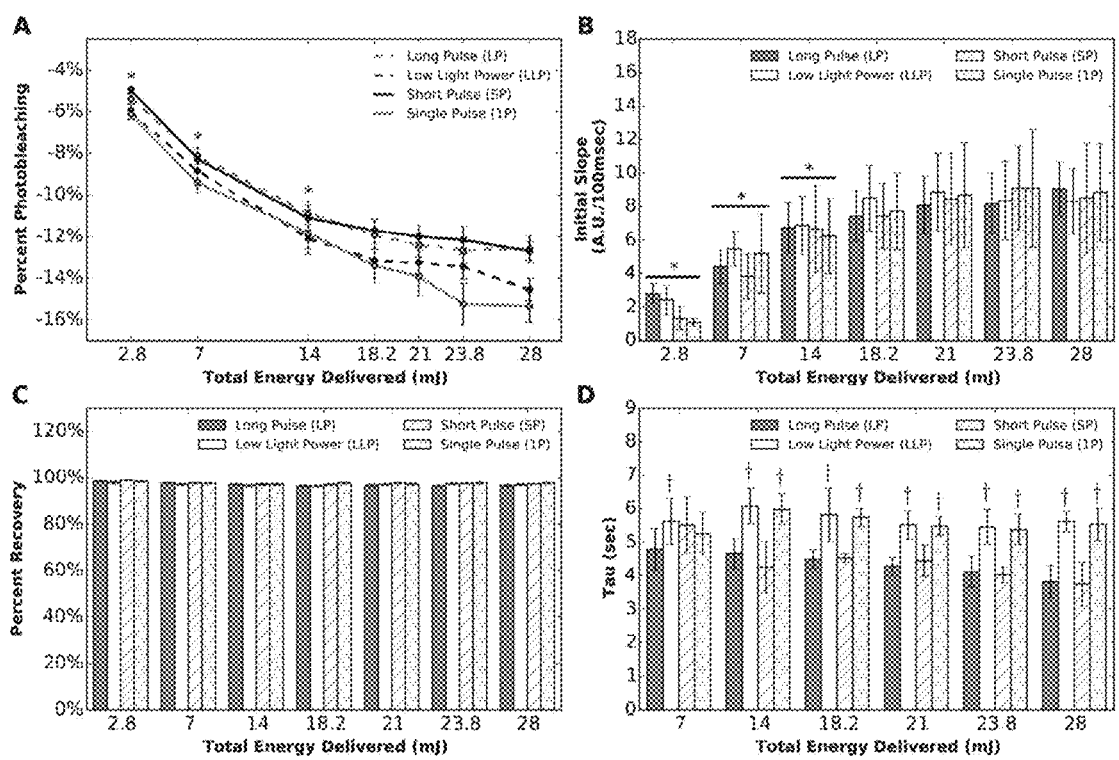
FIG. 2 illustrates the effect of the photobleaching mode (described in Table 1) and total energy delivered (TED) on NADH ED-FRAP measurements during control conditions in perfused hearts (n=5 for each mode at each TED). (Panel A) Percent photobleaching is plotted for each TED between 2.8 and 28 mJ for the four photobleaching modes. For each mode, photobleaching increased until 18.2 mJ, where it reached a maximum. Asterisks indicate significant differences within each mode for comparisons between each TED and a TED of 23.8 mJ. (Panel B) Initial slope of fNADH recovery plotted for TED between 2.8 and 28 mJ for the four photobleaching modes. Initial slope increased within each mode until 18.2 mJ, where it reached a maximum. Asterisks indicate significant differences within each mode for comparisons between each TED and a TED of 23.8 mJ. (Panel C) Percent recovery plotted for TED between 2.8 and 28 mJ for the four photobleaching modes. For all modes, percent recovery approached 100% and was not dependent upon TED ($p>0.05$). (D) Recovery time constant tau plotted for TED between 2.8 and 28 mJ for the four photobleaching modes. Tau varied with photobleaching mode for a particular TED but the effect of TED on tau within each photobleaching mode did not reach statistical significance ($p>0.05$). Crosses indicate significant differences for each TED for tau measured using LLP, SP, and 1P photobleaching modes compared to tau measured using the LP mode.
Figure 9:
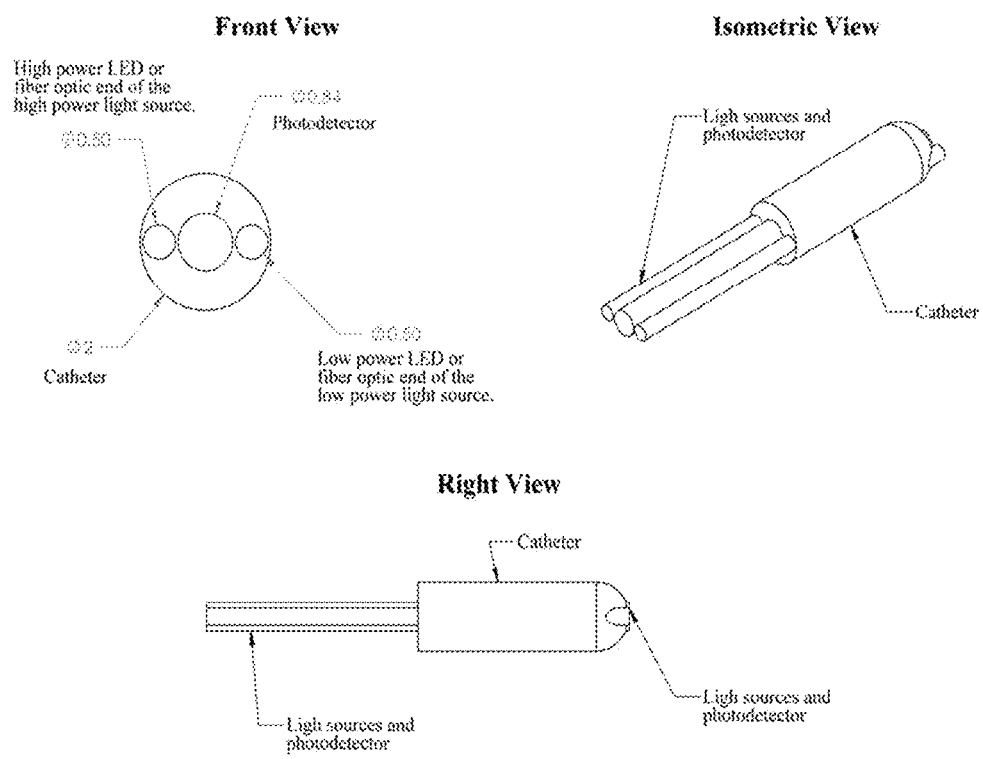

FIG. 9 provides a detailed front right side and isometric schematic of the in-vivo component of the present invention depicted in FIG. 2. Indicated diameters are in millimeters.

DETAILED DESCRIPTION OF THE INVENTION

A system is provided for an optical real-time approach for measuring the rate of NADH production by dehydrogenase enzymes within living tissue. This system represents a novel nondestructive metabolic assay providing improved diagnosis and insight to disease states such as coronary heart disease, heart failure, diabetes, stroke, and cancer. The system also facilitates therapy and management of these disease states. In one aspect the system comprises fiber optic light guides used during catheterization, laparoscopic, or other minimally invasive surgical procedures with high power UV light emitting diodes (LEDs) or high power lamps and UV lasers with the bleaching and recovery parameters disclosed herein. Such fiber optic light guides are disposed within catheters or laparoscopes such that the light emitting components may be present at the proximal end immediately adjacent to the tissue to be illuminated. In other cases the light emitting components may be situated at the distal end of the catheter or laparoscope and the light energy routed along the long axis of the device from sources remote from the tissue to be illuminated. Measuring the activity of dehydrogenase enzymes within cardiac tissue during several altered metabolic states including low temperature, electromechanical uncoupling, and ischemia/reperfusion injury (heart attack) demonstrates the power of the system to make non-destructive, repeatable measurements of dehydrogenase enzyme activity within the same localized volume of tissue. Competing technologies require tissue biopsies and significant tissue post-processing that typically involves enzymatic assessments using optical absorbance of homogenized tissue in a laboratory that specializes in running such assessments. In contrast, the present invention provides real-time non-destructive situ analysis of dehydrogenase enzyme activity within living tissue.

One embodiment of the present invention provides a catheter comprising an ultraviolet illumination device capable of exciting cellular NADH in a localized volume of tissue (i.e., tissue sample) and a fluorescence sensor for acquiring a single measurement or image of the NADH fluorescence of the tissue sample, with each disposed at the distal end of the catheter, and a wire within a trans-axial conduit within the catheter connecting the fluorescence sensor and ultraviolet illumination device to one or more controllers, detectors, and recording devices located at the proximal end of the catheter, such that the detected fluorescence measurement or image shows replenishment of NADH after photobleaching indicative of dehydrogenase enzyme activity within the tissue sample.

Another embodiment of the present invention provides a catheter comprising an ultraviolet illumination device capable of exciting cellular NADH within a localized volume of tissue (i.e., tissue sample) and a fiberscope, each disposed at the distal end of the catheter, and a fluorescence sensor or camera at the proximal end of the catheter for acquiring a single measurement or image of the NADH fluorescence of the tissue sample captured by the fiberscope, such that the detected fluorescence measurement or image shows replenishment of NADH after photobleaching indicative of dehydrogenase enzyme activity in the tissue sample.

In still another embodiment of the present invention a method is provided for imaging a localized volume of tissue (i.e., tissue sample) comprising photobleaching NADH in the tissue sample using a first light energy delivered by an ultraviolet light source, a second light energy source delivered by an ultraviolet light source to illuminate the tissue for imaging, and a fluorescence image detector and means for recording detected images of illuminated photobleached tissue over a period of time. Such light energy may be routed from the light energy source to the tissue and from the tissue to the fluorescence image detector by light guide elements within a catheter or laparoscopic device.

In some embodiments the fluorescence image detector comprises a 460 nm band-pass filter to detect NADH fluorescence within the tissue.

In some embodiments the fluorescence image detector is a charge coupled device (CCD). In some embodiments the fluorescence image detector is an electron multiplying charge coupled device (EMCCD).

In some embodiments the fluorescence detector is a spectrometer that provides a spectrum of fluoresced and reflected light from the tissue, whereby the spectrum includes the wavelengths associated with NADH fluorescence (420-485 nm).

In one embodiment the ultraviolet light source is comprised of one or more light emitting diodes connected to a controller.

In one embodiment the ultraviolet light source is comprised of one or more optical energy delivering bundles traversing the length of a catheter connecting to a light source that may be either a lamp selected from the group of tungsten halogen lamps, mercury lamps, and lasers.

In one embodiment the controller is configured to activate the ultraviolet light source to provide strong photobleaching energy and subsequently a repetition of weaker imaging energies over time, wherein the strong photobleaching energy significantly photobleaches cellular NADH within tissue without harming the tissue.

In some embodiments the strong photobleaching energy delivered to the illuminated tissue volume (i.e., tissue sample) is between about 0 mJ/mm$^2$ to approximately 4.5 mJ/mm$^2$. In preferred embodiments the strong photobleaching energy delivered to the illuminated tissue volume is between about 3 mJ/mm$^2$ to approximately 3.4 mJ/mm$^2$.

In one embodiment the tissue is endocardium, mid-myocardium, or the epicardium of any of the chambers of the heart.

In an embodiment of the present invention the fiberscope is an optical imaging bundle.

In an embodiment of the present invention the distal tip of the catheter has a rounded tip for contacting tissue.

In an embodiment photobleaching of NADH within the tissue comprises temporarily reducing the fluorescence of cellular NADH by at least 10% of the unbleached level without harming the tissue.

In certain embodiments illuminating NADH in the tissue is repeated at intervals to enable observation of the amount of NADH fluorescence over time while the NADH fluorescence recovers after photobleaching.

In embodiments of the present invention the second light energy (used to illuminate the tissue for imaging or recording NADH fluorescence) is weaker than the first light energy (used to photobleach NADH within the tissue).

In many embodiments an additional step of calculating dehydrogenase enzyme kinetics within the tissue, wherein the calculating step is automatically performed by a computing system configured to receive and process the recordings of the illuminated and imaged tissue.

Embodiments of the present invention comprise capturing light emitted (reflected and/or fluoresced) from the illuminated tissue.

Some embodiments of the present invention comprise imaging tissue in real time.

In further embodiments the acquisition of tissue fluorescence after tissue photobleaching forms the basis of a therapeutic procedure for diagnosis or monitoring of normal or pathological conditions.

To determine the physical parameters sufficient for effective photobleaching of tissue without causing tissue damage and the parameters for signal acquisition necessary to measure NADH recovery kinetics, experiments were conducted in vitro on perfused rat hearts. Subject hearts were isolated from Sprague-Dawley rats (315.20±8.83 g, of either sex) after anesthetization via an intraperitoneal injection of Telazol (40 mg/kg). Upon the cessation of pain reflexes, hearts were quickly excised, cannulated via the aorta, and Langendorff perfused at constant pressure (70 mmHg) and temperature (37° C., except as noted) with an oxygenated (95% $O_2$, 5% $CO_2$) Krebs-Henseleit solution, containing, 118 mM NaCl, 4.7 mM KCl, 1.25 mM $CaCl_2$, 0.57 mM $MgSO_4$, 1.17 mM $KH_2PO_4$, 25 mM $NaHCO_3$, 6 mM glucose and 500 mU/L insulin, pH=7.4. For most experiments, the actomyosin ATPase inhibitor 2,3-butanedione monoxime (BDM, 15 mM) was administered to electromechanically uncouple the hearts to minimize motion artifacts during fluorescence imaging (described in detail in [Kay, et al., Am J Physiol Circ Physiol., 291:H1935 (2006)]. An electrocardiogram (ECG) was continuously acquired using a Dagan EX 4-400 bio amplifier (Dagan Corp., Minneapolis, Minn.) and a Power Lab data acquisition system (AD Instruments, Colorado Springs, Colo.).

Figure 4:
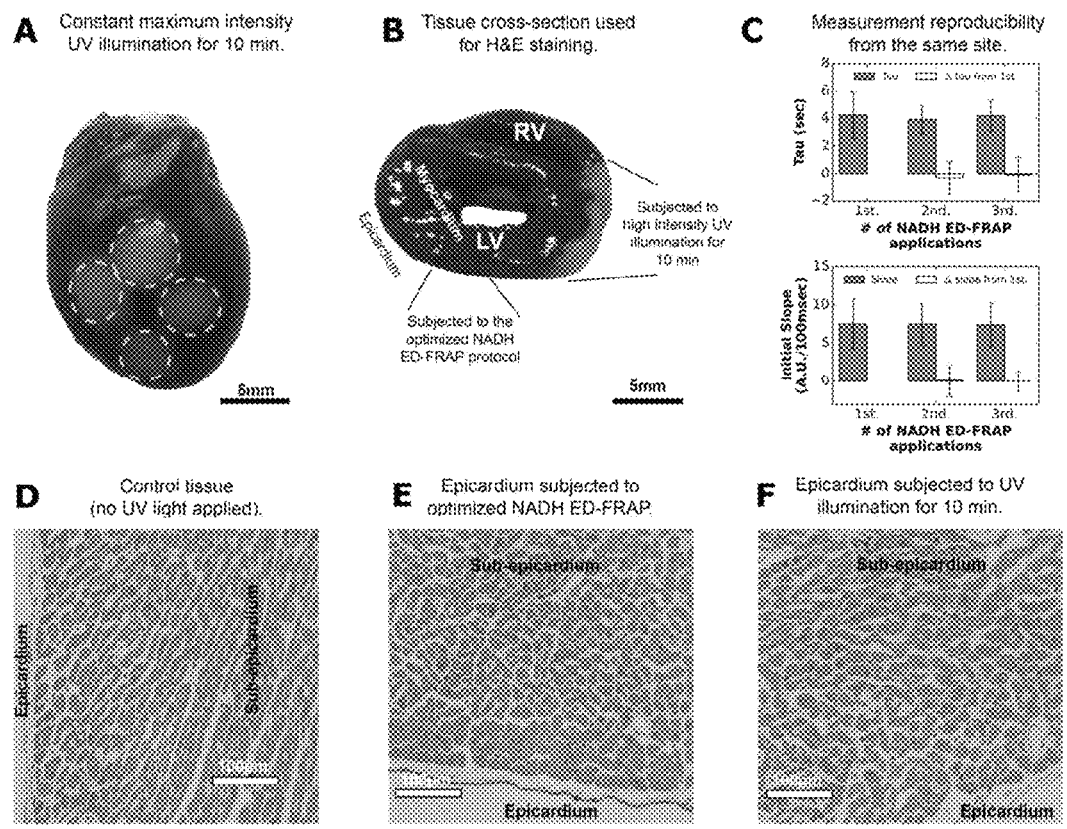
FIG. 4 Assessment of UV illumination effects on tissue viability and cell morphology. (Panel A) After TTC staining of positive controls, non-viable epicardial tissue was revealed at sites exposed to 10 min of continuous UV illumination at max power (500 mW). (Panel B) Cross-section of a heart after TTC staining reveals the transmurality of non-viable tissue in positive controls exposed to high intensity UV illumination for 10 min (500 mW). The high intensity illumination damaged the tissue up to a depth of approximately 0.5 mm. Adjacent tissue exposed to the optimized NADH ED-FRAP protocol (LP mode) remained viable with no visible evidence of epicardial or transmural damage. (Panel C) No difference in measurements of NADH production rate were detected ($p>0.05$) after three applications of NADH ED-FRAP to the same epicardial site. Five minutes elapsed between each measurement. Tau (top) and initial slope of recovery (bottom) were the same after the second and third NADH ED-FRAP measurement compared to the first measurement. Error bars in this panel correspond to standard deviation. (Panel D) H&E staining of an LV short axis section within the area that was not illuminated. As expected, no changes in cellular morphology were observed. (Panel E) H&E staining of an LV short axis section within the area that was exposed to three applications of NADH ED-FRAP using the LP photobleaching mode. No changes in cellular morphology were observed. (F) H&E staining of an LV short axis section within the area that was exposed to high intensity UV illumination for 10 min (500 mW). No changes in cellular morphology were observed even though TTC staining revealed that this tissue was not viable, as shown in Panel B.

Initial NADH ED-FRAP illumination and imaging parameters were determined. Two UV LED spotlights, a low power PLS-0365-030-S and a high power LCS-0365-11-22 (Mightex Systems, Pleasanton, Calif.) provided light (367.50±5.50 nm) to illuminate the epicardium. The low power spotlight (1.5 mW) was used for continuous NADH fluorescence (fNADH) imaging and the high power spotlight (500 mW) was used to photobleach NADH. The high power spotlight illuminated 4 epicardial regions, each with an epicardial surface area of approximately 7 $mm^2$ (FIG. 4A). Prior to each experiment, a single image was acquired with the high power spotlight at low power (0.71 mW) to locate the 4 regions for subsequent analysis. Emitted epicardial fluorescence was band pass filtered (475±25 nm, peak 460 nm (based on the values reported by Chance, et al., [Chance, et al., J Biol Chem., 254:4764 (1979)]) and imaged at 10 Hz using an iXon DV860 CCD camera (Andor USA, Concord Mass.). A background image (no lights) and a reference image (low power light source on, but no heart) were acquired before beginning each study. These images were stored and used for off-line analysis to automatically remove the baseline counts for each pixel. The lights and camera were synchronized using a custom LabVIEW (National Instruments, Austin Tex.) program. A typical NADH ED-FRAP protocol was: 5 sec of baseline (control) imaging, a brief period of NADH photobleaching (0.30-8.0 sec, described below), and 95 sec of imaging to record fluorescence recovery (FIG. 4B). fNADH was continuously acquired after the photobleaching process to observe the fluorescence recovery. One-dimensional spatial fNADH profiles were computed by interpolating fNADH along a user-defined 3.3 mm long line (one pixel wide) that passed through a photobleached area (FIG. 4C).

Based on the results observed under the conditions described above NADH ED-FRAP parameters were further optimized as described. Multiple variables were studied to determine optimal photobleaching parameters. The total energy delivered (TED) for photobleaching was optimized by increasing TED from 2.8 to 28 mJ while analyzing 4 key parameters (FIG. 4D): 1) Percent photobleaching, the drop in fNADH that occurs immediately following illumination with high-intensity UV light; 2) Tau, the time constant of the rise ($\tau$) of fNADH after photobleaching; 3) Initial slope, the recovery rate of fNADH during the first second after photobleaching; and 4) Percent recovery, the degree to which fNADH recovered to baseline.

Approaches for delivering optimal TED for photobleaching were defined to study how TED might best be applied. As such, four photobleaching "modes" were defined with specific light power, duty cycle, and pulse widths (Table 1), with each providing equal TED. For example, while maintaining TED at 23.8 mJ, the effect of decreasing the length of each individual light pulse was tested by decreasing the pulse width from 6 msec (Long Pulse, LP) to 200 µsec (Short Pulse, SP), while light power (500 mW), duty cycle (50%), and total bleaching time (5.1 sec) remained constant between the two conditions (Table 1). Next, 375 mW (Low Light Power, LLP) was used to measure the effect of reducing the light power by 25%. Duty cycle remained at 50% with a pulse width of 6 msec. This increased total photobleaching time to 6.8 sec while maintaining TED at 23.8 mJ (Table 1). Finally, the effect of a single pulse (1P) for photobleaching was tested, which dropped total bleaching time to 2.55 sec while maintaining a TED of 23.8 mJ. Each photobleaching mode (LP, SP, LLP, and 1P) was tested at each TED (2.8 to 28 mJ). The number of pulses, duty cycle, and pulse width for each photobleaching mode was controlled using our LabVIEW program, which also synchronized with the camera and ensured that the camera did not acquire images during photobleaching to prevent damage to the CCD.

TABLE 1

Parameters for the four modes of photobleaching light applied during photobleaching optimization experiments (see FIG. 2).

|  | Light Power | Duty Cycle | Pulse Width | Energy Per Pulse | Total Bleaching Time | No. Pulses | Total Energy Delivered |
|---|---|---|---|---|---|---|---|
| Long Pulse (LP) | 500 mW | 50% | 6 msec | 28 µJ | 5.1 sec | 850 | 23.8 mJ |
| Short Pulse (SP) | 500 mW | 50% | 200 µsec | 0.934 µJ | 5.1 sec | 25482 | 23.8 mJ |

TABLE 1-continued

Parameters for the four modes of photobleaching light applied during photobleaching optimization experiments (see FIG. 2).

| | Light Power | Duty Cycle | Pulse Width | Energy Per Pulse | Total Bleaching Time | No. Pulses | Total Energy Delivered |
|---|---|---|---|---|---|---|---|
| Low Light Power (LLP) | 375 mW | 50% | 6 msec | 21 µJ | 6.8 sec | 1132 | 23.8 mJ |
| Single Pulse (1P) | 500 mW | 100% | 1 pulse | Continuous | 2.55 sec | 1 | 23.8 mJ |

Tissue viability was measured as described. At the end of the ED-FRAP protocol, hearts were incubated in a triphenyltetrazolium chloride (TTC) solution at 37° C. for 10 min to determine if NADH ED-FRAP damaged the tissue. TTC stains metabolically active tissue a deep red color, with metabolically inactive or damaged tissue presenting as a pale tan color. Tissue damage was assessed in this way for three hearts from each protocol in Table 1.

While percent photobleaching was calculated with respect to the baseline fNADH, the range of fluorescence from fully oxidized to fully reduced NADH was measured to determine the percentage of the total NADH pool that was photobleached. A baseline fNADH was acquired before terminating flow to the aorta, resulting in global ischemia and full reduction of the mitochondrial NADH pool (FIG. 4B). fNADH was acquired until fluorescence plateaued. In other hearts, after acquiring baseline (control) fNADH, carbonyl cyanide m-chlorophenylhydrazone (CCCP, 10 µM) was added to the perfusate to dissipate the mitochondrial proton gradient, oxidizing NADH, causing the fNADH signal to drop. The NADH pool was considered to be fully oxidized when the fNADH signal plateaued and illumination with the high power UV LED did not cause an additional drop in fNADH. After acquiring these approximate boundaries of fNADH, the data were normalized to the minimum fNADH signal.

The effect of temperature was examined as described. Low temperatures slow the rate of enzyme-catalyzed reactions so whether NADH ED-FRAP would reveal the effect of a drop in perfusate temperature on the rate of NADH production in perfused hearts was examined. These experiments were performed using the LP mode of photobleaching with a TED of 23.8 mJ (Table 1). Perfusate temperature was set at either 22±0.18, or 30±0.16, or 36.6±0.11° C. for each study. The rate of fNADH recovery was measured after multiple rounds of photobleaching at each perfusate temperature.

Glutamate dehydrogenase (GDH) activity was determined using enriched mitochondrial fractions to correlate the rate of fNADH recovery measured after photobleaching with the activity of an NADH producing enzyme that resides within the mitochondria. Enriched mitochondrial fractions were extracted from ventricular tissue and 0.08-0.13 µg of protein was added to a cuvette containing: 50 mM TEA, 2.5 mM EDTA, 100 mM ammonium acetate, 1 mM ADP, 0.2 mM NADH, and 2 kU/L lactate dehydrogenase, in a final volume of 1 mL, pH=7.6. Background absorbance was measured at 340 nm for 1 min in a SpectraMax Plus 384 spectrophotometer (Molecular Devices, Sunnyvale, Calif.). The addition of 2-oxogluterate (7 mM) initiated substrate-dependent activity and $A_{340}$ was measured at 340 nm for 2 min. GDH activity was calculated using an NADH millimolar extinction coefficient of 6.23. Average temperatures for GDH activity measurements were 22±0.01, 30.02±0.01, and 37±0.01° C.

The actomyosin ATPase is a major consumer of myocyte ATP and its rate of ATP hydrolysis modulates the rate of mitochondrial NADH production. The impact of actomyosin ATPase activity on fNADH recovery after photobleaching was measured. Before administering the actomyosin ATPase inhibitor BDM, NADH ED-FRAP was applied to contracting perfused hearts. BDM was then administered and hearts were monitored until the cessation of contractions and a stable heart rate were observed. NADH ED-FRAP was performed again to compare fNADH recovery kinetics before and after actomyosin ATPase inhibition.

Acute ischemia/reperfusion injury has been reported to diminish mitochondrial ATP production. If so, then the rate of NADH production may also be lower after ischemia/reperfusion injury. We tested this hypothesis in a separate set of perfused heart studies using NADH ED-FRAP. Baseline fNADH recovery kinetics were measured before aortic flow was halted for 20 min. Hearts were reperfused for 10 min, after which fNADH recovery kinetics were measured via NADH ED-FRAP. fNADH recovery kinetics measured before and after global ischemia/reperfusion were then compared.

EXAMPLES

The following examples illustrate the scope of the invention. Specific elements of the examples are for descriptive purposes only and are not intended to limit the scope of the invention. Those skilled in the art could develop equivalent methods and utilize comparable materials that are within the scope of the invention.

Example 1

Effects of Different TED on NADH ED-FRAP

A minimum TED must be achieved to provide repeatable photobleaching. Increasing TED from 2.8 to 18.2 mJ increased percent photobleaching for each photobleaching mode (LP, SP, LLP and 1P) (FIG. 2A). As TED increased from 18.2 to 28 mJ, there was little increase in the percent photobleaching, indicating maximal photobleaching with our optical system. For all modes, percent photobleaching for TED greater than 18.2 mJ was compared to percent photobleaching at a TED of 23.8 mJ and the differences were not significant (p>0.05), indicating that maximal photobleaching could be assured with a TED of 23.8 mJ. The exception was when TED was delivered using the 1P mode: an increase in TED above 18.2 mJ increased percent photobleaching beyond that of the SP and LP modes (p<0.05) (FIG. 2A). However, for the 1P mode, percent photobleaching for TED equal to or greater than 18.2 mJ was not significantly greater than that of 23.8 mJ.

The initial slope of recovery was also dependent upon the TED. Initial slope increased as TED was increased from 2.8 to 14 mJ across all photobleaching modes, with initial slope remaining constant as TED was increased from 18.2 to 28 mJ (FIG. 2B). Unlike percent photobleaching and initial slope, the percent recovery of fNADH was very consistent for all TEDs (FIG. 2C). When grouping all photobleaching modes together, percent recovery was 98.4±0.45% at the lowest TED, and only decreased slightly to 97.2±0.31% at the highest TED.

Significant variability was observed across photobleaching modes in measurements of the recovery time constant tau (FIG. 2D). For all modes at a TED greater than 7 mJ, tau was consistently shorter when the TED was delivered with the LP or SP modes compared to LLP and 1 P modes (FIG. 2D) ($p<0.001$). Tau for LLP and 1P modes was significantly longer than that of LP ($p<0.001$), meaning fNADH recovery was slower for these photobleaching modes. These differences occurred despite equal initial slopes of recovery for all photobleaching modes at the same TED (FIG. 2B). Comparing tau within individual photobleaching modes across all TEDs did not indicate that TED had a significant effect on tau.

Example 2

Effects of NADH ED-FRAP on Tissue Viability

Figure 3:
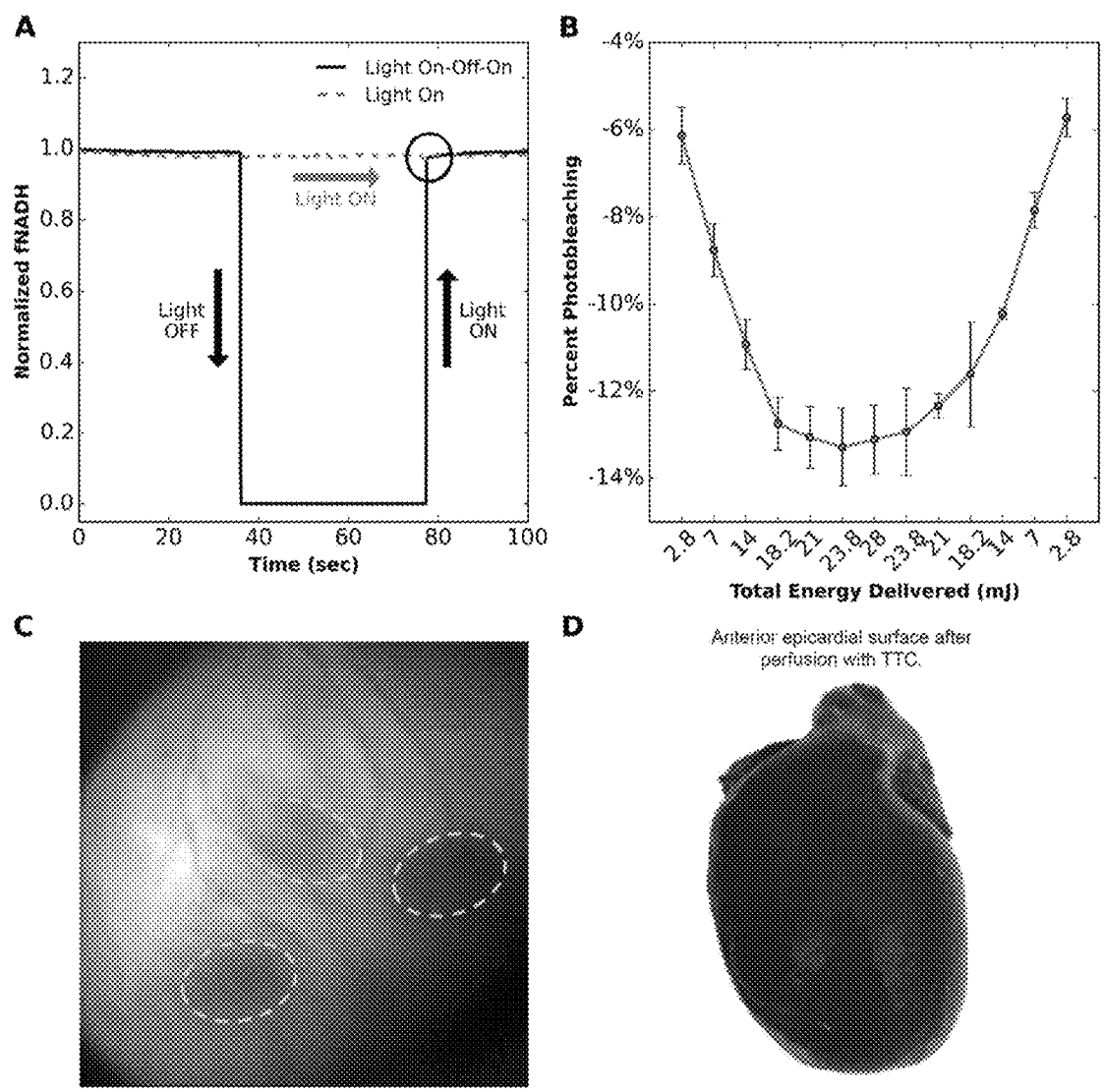
FIG. 3 Sustained NADH photolysis and tissue viability after NADH ED-FRAP. (Panel A) Normalized fNADH is plotted to illustrate that low power UV illumination (1.5 mW) used to image fNADH does not cause measurable NADH photobleaching in excised perfused hearts. A sequence of light on-off-on shows that fNADH after continuous illumination matches that of fNADH immediately after a 40 sec interval of darkness (circled). (Panel B) Percent photobleaching is not altered by previous applications of photobleaching light (LP mode). Results are shown for a "round trip" experiment where TED was increased from 2.8 to 28 mJ then decreased from 28 to 2.3 mJ for the same region of tissue (n=3 hearts). (C) Sustained NADH photolysis was observed (indicated by a sustained drop in fNADH) after applying six rounds of high energy (18.2-28 mJ, LP mode) to the same areas of tissue (circled). (Panel D) Less than six applications of high energy (18.2-28 mJ, LP mode) to the same region of tissue did not affect tissue viability, as evidenced in the image shown by the absence of pale epicardial tissue within photobleached regions after TTC staining.

Two studies were conducted to verify that the low power UV illumination (1.5 mW) used to image epicardial fNADH would not cause tissue photo damage or significant NADH photobleaching. First, fNADH was continuously acquired from an epicardial region of interest while illuminating the epicardium for 35 sec, then the low power UV light was turned off for 40 sec and back on for another 35 sec. fNADH was acquired again from the same region of interest during 100 sec of constant illumination, which is the time typically required for one NADH ED-FRAP measurement. fNADH signals from a study are shown in FIG. 3A, which indicate that NADH fluorescence is not lower when the low power UV light was on compared to what it would be if the light were off (circled region in FIG. 3A). Similar studies were completed by Combs and Balaban in isolated myocytes and demonstrated a slow constant decline of fNADH during steady-state UV illumination, mainly due to the balance between the net product of NADH photolysis and its metabolic production2. In contrast, our measurements in perfused hearts indicate stable fNADH during steady-state illumination without detectable photobleaching caused by low power UV illumination.

The second measurement involved examining whether epicardial tissue remained viable after several rounds of photobleaching, even after the maximal TED of 28 mJ was applied. Percent photobleaching, tau, initial slope of recovery, and percent recovery in a photobleached region were not altered by previous NADH ED-FRAP applications. This is shown for percent photobleaching in FIG. 3B, where TED for a single site was increased from 2.8 to 28 mJ then decreased from 28 to 2.8 mJ. This "round-trip" NADH ED-FRAP shows that photobleaching percentage is dependent upon the amount of energy imparted to the heart but not the order in which it is applied. However, we did observe that repeated application of high power UV light to the same area caused irreversible NADH photolysis. This is evident after 6-8 rounds of ED-FRAP at high energies (18.2-28 mJ), as shown in FIG. 3C. Four applications of such high energy caused a sustained (NADH loss of up to 10% with respect to the first application. Even so, triphenyltetrazolium chloride (TTC) staining indicated that the tissue remained viable (FIG. 3D). Altogether, these results indicate that NADH ED-FRAP at TED between 18.2-28 mJ should be limited to no more than three or four applications per site to avoid sustained NADH photolysis.

Epicardial tissue exposed to the LP photobleaching mode did not exhibit evidence of cellular damage in either TTC staining assessments (FIGS. 3D and 4B) or haematoxylin and eosin (H&E) cellular histology assessments (FIG. 4E). NADH ED-FRAP was repeated three times at same epicardial site to further confirm that the LP photobleaching mode did not detrimentally impact tissue viability and measurement repeatability. Tau and initial slope of recovery were compared after each application (FIG. 4C). No significant difference ($p>0.05$) was detected when measurements from the second and third application were compared to the first application. This suggests that tissue viability was not detrimentally altered after three or less applications of NADH ED-FRAP. As a positive control, other hearts were subjected to 10 min of continuous UV illumination at the maximum LED power (500 mW). TTC and H&E assessments were repeated. As expected, TTC staining revealed metabolically inactive tissue within the areas that were subjected to the 10 min of 500 mW UV illumination (FIGS. 4A, B). However, histological analysis did not reveal cellular morphology changes and many nuclei maintained a highly defined and normal shape (FIG. 4F).

Example 3

Effect of Temperature on NADH ED-FRAP

It is generally understood that enzyme activity is positively correlated with temperature, with dependencies ranging from sub-freezing to high temperatures. This correlation is the basis for therapeutic hypothermia, an approach used for patients suffering from cardiac arrest and during cardiac surgeries that require cardiopulmonary bypass. When myocardial temperature is lowered, heart rate, contractile force, oxygen consumption, and, ultimately, ATP utilization all drop dramatically. A reduction in myocardial temperature decreases both the steady state utilization and production rate of ATP, as well as decreases the upstream utilization and production of NADH.

Figure 5:
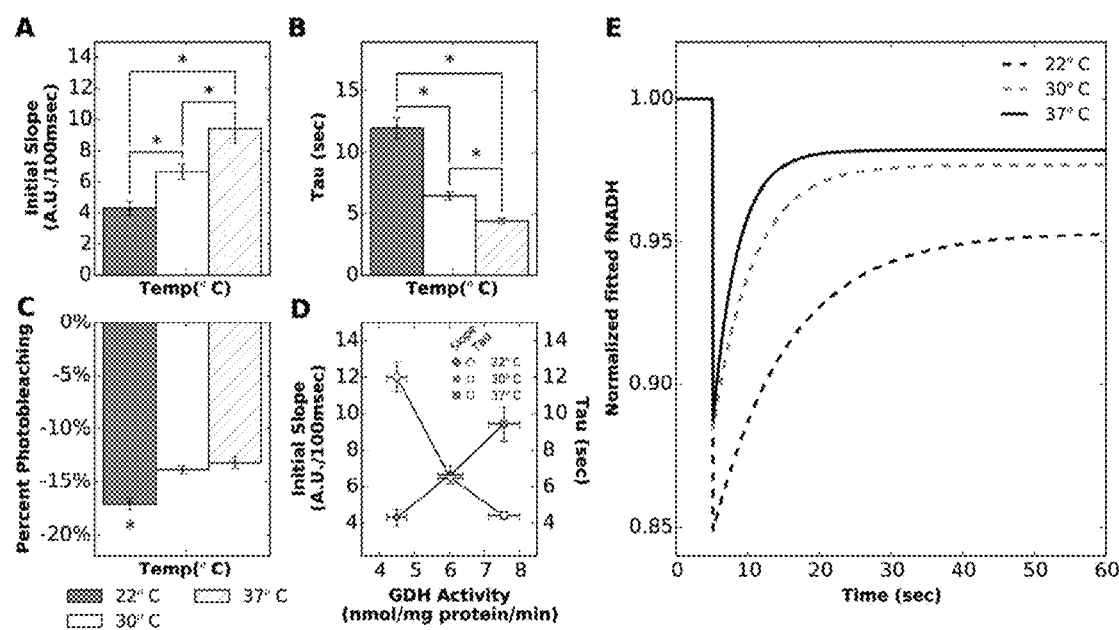
FIG. 5 NADH ED-FRAP measurements (LP mode) for hearts perfused at three temperatures. Hearts were electromechanically uncoupled with BDM. (Panel A) The initial slope of fNADH recovery increases with temperature ($p<0.001$, n=5). (Panel B) The time constant of fNADH recovery (tau) drops with increasing temperature ($p<0.001$, n=5) (Panel C) Percent photobleaching is greater at 22° C. ($p<0.001$, n=5) but not significantly different at 30 & 37° C. (Panel D) Initial slope and tau measured from hearts perfused at 22, 30, and 37° C. are plotted with GDH activity (n=4) measured at the same temperatures. (Panel E) Representative fNADH data acquired during NADH ED-FRAP were fitted ('y' in Equation 4) and plotted for the three temperatures studied.

Hearts were perfused at three temperatures ranging from hypothermic to normothermic conditions to evaluate the effect of perfusion temperature on NADH production rate. The rate of fNADH recovery after photobleaching increased as temperature increased from 22 to 37° C. (FIGS. 5A and B). Although percent photobleaching was equal at 30 and 37° C., there was more photobleaching at 22° C. compared to the higher temperatures (FIG. 5C). This is likely due to the fact that, during photobleaching, NADH is still being produced however at the low temperature the rate of NADH production is so low that photobleaching can achieve a higher level of NADH photolysis. Of note is that fNADH only recovered to 95.1±0.45% at 22° C. compared to 97.0±0.34% and 97.0±0.37% at 30 and 37° C., respectively.

Indeed, the recovery kinetics of fNADH dropped as temperature dropped, indicating a significant decrease in NADH production with the lower metabolic demand of low temperatures (5E). Overall, the relationship between initial slope and temperature (FIG. 5A) and tau and temperature (FIG. 5B) was proportional, although tau appeared to increase more between 30 and 22° C. than between 37 and 30° C., indicating that the relationship may have an exponential component. At low temperatures, slower fNADH recovery kinetics corresponded to lower GDH activities (FIG. 5D).

Likewise, enriched mitochondrial fractions were subjected to the 3 temperatures above to determine GDH activity. GDH activity increased from 4.5±0.28 nmol/mg protein/min at 22° C. to 6.0±0.35 and 7.3±0.46 nmol/mg protein/min at 30 and 37° C., respectively. These values tightly correlated with NADH ED-FRAP initial slope and tau (FIG. 5D). GDH is a mitochondrial enzyme that catalyzes the reversible inter-conversion of glutamate to α-ketoglutarate and ammonia using NADPH and NADH as cofactors. As such, GDH activity is associated with the consumption of glutamate by GDH, generating NADH. The progressive reduction of GDH activity as temperature was lowered, as measured using a standard molecular assay, indicates that fNADH recovery kinetics during NADH ED-FRAP mirrors changes (FIG. 5D) in the activity of one of the major NADH producing enzymes in the mitochondria.

Example 4

Effect of Contraction on NADH ED-FRAP

Figure 6:
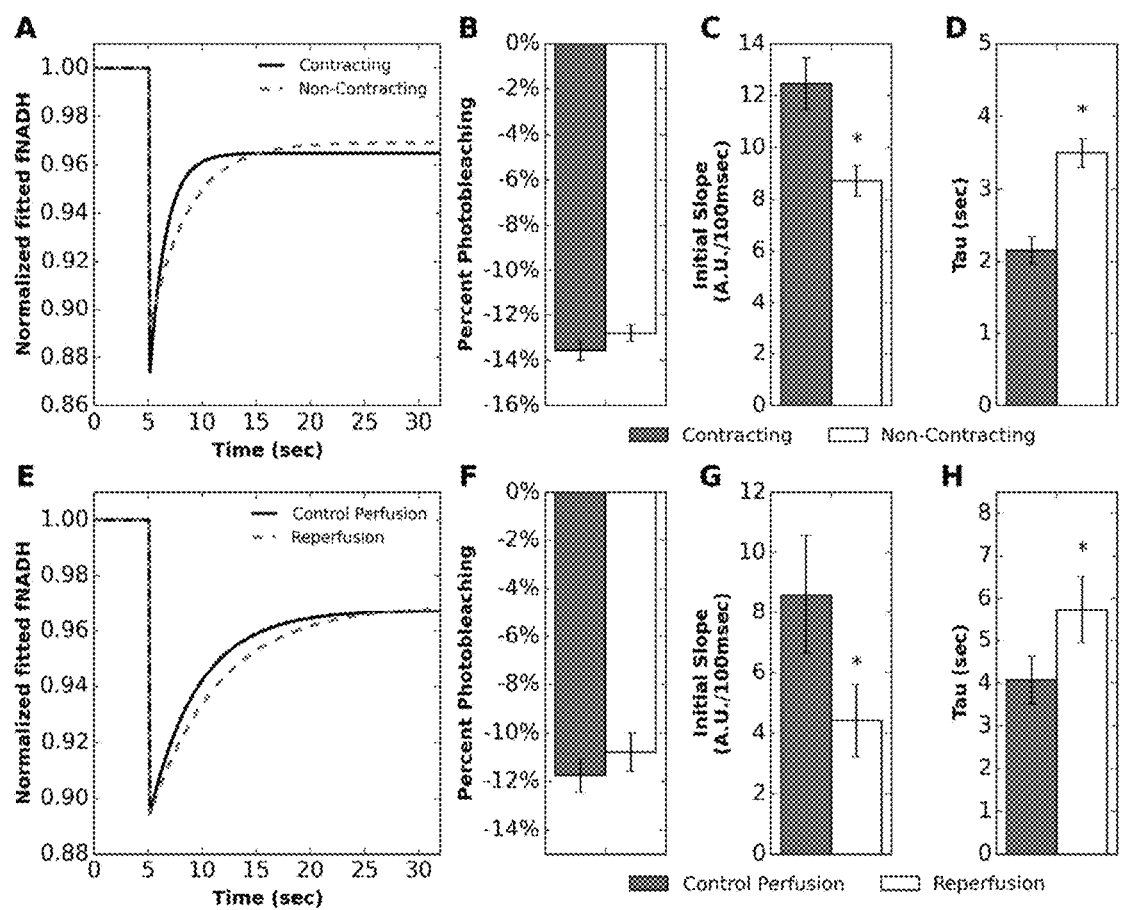
FIG. 6 NADH ED-FRAP measurements (LP mode) showing the effect of contraction (top row) and ischemia/reperfusion injury (bottom row) on the rate of NADH production in perfused hearts. (Panel A) Representative fNADH data were fitted and plotted for NADH ED-FRAP applied to contracting hearts and non-contracting hearts electromechanically uncoupling with BDM. (Panel B) Percent photobleaching was not significantly different between contracting and non-contracting hearts ($p>0.05$, n=6). (Panel C) The initial slope of fNADH recovery was significantly higher in contracting hearts ($p=0.015$, n=6). (Panel D) The time constant of fNADH recovery (tau) was significantly shorter in contracting hearts ($p<0.001$, n=6). (Panel E) Representative fNADH data were normalized and plotted for NADH ED-FRAP applied before ischemia and 10 min after reperfusion. Hearts were electromechanically uncoupled with BDM. (Panel F) Percent photobleaching was not significantly different before ischemia and after reperfusion ($p>0.05$, n=5). (Panel G) The initial slope of fNADH recovery was significantly lower after reperfusion ($p=0.04$, n=5). (Panel H) The time constant of fNADH recovery (tau) was significantly longer after reperfusion ($p=0.049$, n=5).

The effect of actomyosin ATPase inhibition was studied using NADH ED-FRAP to determine if the rate of NADH production, as measured by fNADH recovery after photobleaching, would correlate with a reduction in myocardial energy consumption caused by reduced actomyosin ATPase activity. Typical fNADH recovery curves for contracting and non-contracting hearts after actomyosin ATPase inhibition are shown in FIG. 6A. The initial slope was greater in hearts before inhibition (FIG. 6C) and that tau was shorter (FIG. 6D), demonstrating increased NADH and ATP production rates when the heart is performing mechanical contraction. Interestingly, percent photobleaching was greater in contracting than noncontracting hearts (−14.3±0.48% vs −11.7±0.48%) (FIG. 6B). It was predicted that photobleaching would be greater in non-contracting hearts because NADH production rate would be slower. Percent recovery was also slightly lower in contracting compared to noncontracting hearts (95±0.35% vs 97±0.47%).

Three main processes consume a majority of myocardial energy: actomyosin crossbridge cycling (~76%), calcium transport (~15%), and the maintenance of sarcolemmal potential by the Na+/K+ ATPase (~9%) [see Kuzmiak-Glancy, S., et al., Exp Physiol., 603-616 (2015)]. Thus, inhibition of the actomyosin ATPase significantly diminishes myocardial energy consumption, which slows ATP production and slows upstream NADH production. In contracting hearts fNADH rises rapidly after the termination of flow to the aorta, reaching a plateau (full reduction of NADH) within ~90 sec. In contrast, in electromechanically uncoupled hearts NADH accumulation during ischemia is much slower and reaches a plateau after 5-10 min (Kay, et al., Am J Physiol Circ Physiol., 294:H2400 (2008)]. These differences in the rate of NADH production between contracting and electromechanically uncoupled hearts were confirmed by the higher initial slopes and shorter values of tau that were measured via NADH ED-FRAP (FIGS. 6C and D). Although the motion of contraction introduced a non-negligible level of oscillation in fluorescence acquired during NADH ED-FRAP, the oscillation frequency was much higher than the slower average rise of fNADH, providing for adequate analysis of fluorescence recovery kinetics.

Example 5

Effect of Ischemia/Reperfusion on NADH ED-FRAP

Acute ischemia/reperfusion injury was examined using NADH ED-FRAP to determine if the rate of NADH production, as measured by fNADH recovery after photobleaching, was impaired after reperfusion. Typical fNADH recovery curves before and after injury are shown in FIG. 6E. The initial rate of recovery was almost two times faster before ischemia than after reperfusion (8.17±1.82 vs 4.41±1.19 A.U./100 msec, respectively) (FIG. 6G). The fNADH recovery time constant tau was also significantly longer after reperfusion than before ischemia (5.73±0.79 vs 4.12±0.46 sec, respectively) (FIG. 6H). Percent photobleaching was slightly lower after reperfusion but not significantly different the value before ischemia (FIG. 6F).

NADH levels rise and fatty acid and carbohydrate oxidation are halted when mitochondrial oxygen availability is compromised during ischemia. After reperfusion, cardiac energy production remains compromised, likely due to an imbalance of glucose oxidation and glycolysis that could be the result of altered energy utilization [Kantor, Dyck and Lopaschuk, Am J Med Sci., 318:3 (1999)]. The results reported here are consistent with the previous studies, wherein a significant difference before and after acute ischemia/reperfusion injury is observed in both the initial slope of fNADH recovery (FIG. 6G) and tau (FIG. 6H). These data provide the interesting observation that, even after 10 min of reperfusion, the rate of NADH production remained lower than the pre-ischemic level. Furthermore, low levels of NADH production were maintained even though heart rate returned to the pre-ischemic level: 196±12.1 bpm before ischemia and 183±12.1 bpm after ischemia (not significantly different). These observations confirm the sustained effects of ischemia/reperfusion injury on isolated perfused hearts and that NADH ED-FRAP is a useful approach for measuring NADH production after metabolic insults.

Example 6

Optimal NADH ED-FRAP Implementation

As presented in FIG. 3B, percent photobleaching and the initial slope of fNADH recovery were dependent upon TED values below 18.2 mJ. Percent photobleaching and initial slope were not significantly different for TED values above 18.2 mJ. Similar results were reported by Combs and Balaban in isolated cardiac myocytes [Combs and Balaban, (2001)]. In those studies, the recovery rate of fNADH increased when the level of NADH photolysis increased by either changing the overall power of the laser or the number photobleaching pulses. These results indicate that a standard mode of photobleaching should be used for all NADH ED-FRAP measurements in a set of experiments to avoid measurement artifacts. These results also indicate that percent recovery and tau are likely not as sensitive to TED (FIGS. 2C and D). Although tau was dependent upon the photobleaching mode, the effect of TED on tau within each photobleaching mode did not reach statistical significance (FIG. 2D). This suggests that tau could be a more robust indicator of dehydrogenase activity when systematic delivery of a specific TED cannot be guaranteed.

Analysis of percent photobleaching, initial slope, tau, and percent recovery for all photobleaching modes, indicates the long pulse (LP) mode (Table 1) produces the best results. With this mode, TED is situated within the percent photobleaching plateau (FIG. 2A) and the pulse width of 6 msec is compatible with most software and hardware for the development of custom NADH ED-FRAP applications. Shorter pulse widths, such as 200 μsec for the SP mode, often require specialized hardware and software.

The results also indicate that low power UV illumination (1.5 mW) used to image (NADH does not cause detectable photobleaching of epicardial tissue (FIG. 3D). This may be the result of an increase in NADH production to balance NADH photolysis or simply the result of negligible NADH photolysis by such low power light. We have also shown that high power UV illumination (500 mW) applied using the LP photobleaching mode is non-destructive and that several NADH ED-FRAP measurements can be obtained from the same tissue without significantly altering subsequent measurements (FIGS. 3B and D).

Example 7

Device for In Situ NADH ED-FRAP

Figure 7:
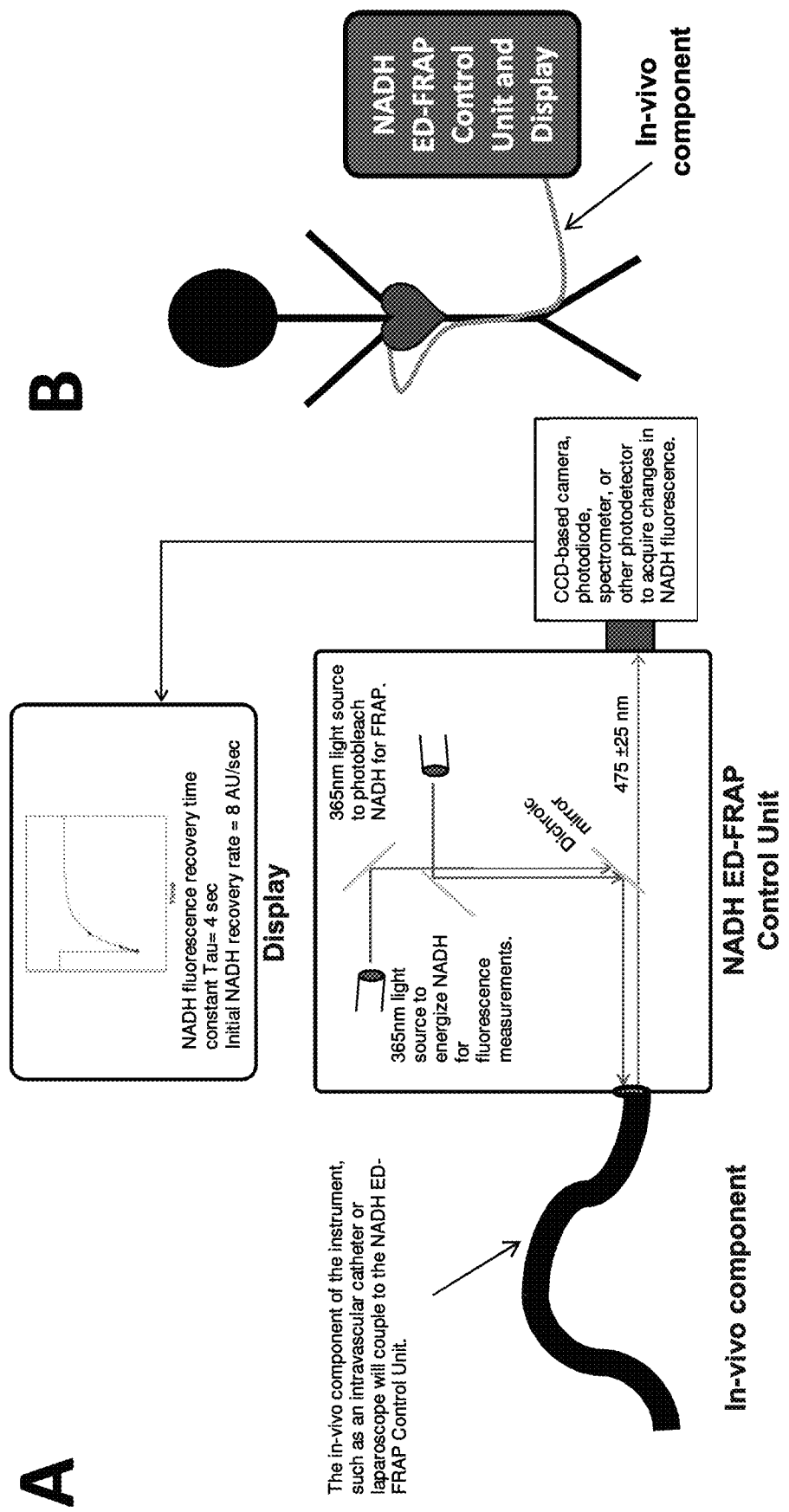
FIG. 7 represents certain embodiments of an NADH enzyme-dependent fluorescence recovery after photobleaching (ED-FRAP) instrument suitable for clinical measurements of tissue metabolic rate. Panel A indicates the device comprises an in-vivo component for accessing tissue via a minimally invasive surgical approach and ex-vivo components comprised of a control unit and display. The instrument acquires NADH fluorescence from in-vivo tissues at high temporal resolution while photobleaching local NADH stores within the mitochondria of tissues within the localized measurement region using a high-power short-duration UV pulse. The recovery of the NADH fluorescence of the tissue within the localized measurement region is acquired before and after photobleaching using low-intensity UV illumination. These data are used to measure the recovery rate of NADH fluorescence, which is proportional to the mitochondrial production rate of NADH. Panel B presents a simplified schematic illustrating how the NADH ED-FRAP instrument is used to measure the metabolic rate of cardiac tissue. A cardiac catheter is inserted into a large peripheral vein, advanced into the heart, the distal tip placed against the endocardium, a high power UV pulse train photobleaches mitochondrial NADH, and the NADH recovery kinetics measured and displayed on the display unit of the NADH ED-FRAP control unit.

The photobleaching and low power UV illumination settings described above are suited for use with optical energy delivering bundles comprising, without limitation, optical fibers or liquid light guides. In one configuration the high energy photobleaching light energy is delivered from an external source controller to an optical fiber bundle sheathed within a catheter or laparoscopic device that is introduced into a living subject and directed to target tissues in situ (FIG. 7). Low power UV illumination light energy can also be produced by an external source controller and routed to the photobleached tissue within the living subject via parallel optical fiber bundles within the catheter. Likewise, the fluorescent signal produced by the NADH under influence of low power UV illumination can be detected by routing the fluorescent signal to an external detector via similar optical fiber bundles. In this fashion NADH ED-FRAP can be carried out on internal tissues within living subjects.

Figure 8:
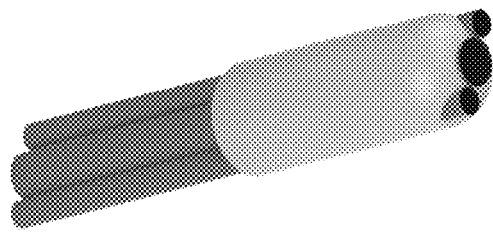
FIG. 8 presents two views of a 3D space filling model showing one embodiment of the in-vivo component of the present invention, wherein individual conduits (dark gray)
Figure 8:
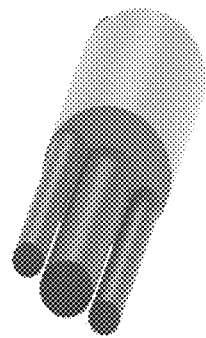

Alternative configurations may include low power UV illumination sources, such as small LEDs, embedded in the distal tip of the catheter or laparoscopic device adjacent to the tissue. Some configurations include small CCD camera elements embedded in the distal end of the catheter or laparoscopic device. Some configurations include both a low power UV illumination source and a CCD camera present on the distal end of the device. The tip of such catheter or laparoscopic device is rounded for allowing close contact with the target tissue and the light energy and detector outlets are arrayed as shown in FIGS. 8 and 9.

What is claimed is:

1. A catheter to monitor enzyme activity in tissue comprising:
an ultraviolet illumination device disposed at a distal end of the catheter for exciting cellular, including mitochondrial, NADH of the tissue, wherein the ultraviolet illumination device comprises at least two ultraviolet light-emitting diodes (LEDs) including a first ultraviolet LED to photobleach NADH in the tissue and a second ultraviolet LED to thereafter illuminate the NADH in the tissue for fluorescence imaging;
a fluorescence sensor at the distal end of the catheter for acquiring a single measurement or an image of NADH fluorescence of the tissue; and
a wire disposed inside a trans-axial conduit within the catheter to connect the fluorescence sensor to a controller located at a proximal end of the catheter,
wherein a detected fluorescence measurement or image shows a replenishment of fluorescent NADH after photobleaching indicative of cellular dehydrogenase enzyme kinetics within the tissue.

2. The catheter of claim 1, wherein the fluorescence sensor includes a 460 nm band-pass filter to detect the NADH fluorescence from the tissue.

3. The catheter of claim 1, wherein the fluorescence sensor is a CCD or EMCCD arranged in the center of a tip of the catheter.

4. The catheter of claim 1, wherein the fluorescence sensor is arranged in the center of a tip of the catheter and is coupled to a spectrophotometer.

5. The catheter of claim 1, wherein the ultraviolet illumination device is connected by means of solid-state electronic components to a controller at the proximal end of the catheter, said controller configured to power and control the ultraviolet illumination device.

6. The catheter of claim 1, wherein the ultraviolet illumination device is comprised of one or more ends of one or more optical energy delivering bundles, said one or more optical energy delivering bundles traversing an interior of the catheter and connecting on the proximal end of the catheter with the first ultraviolet LED and the second ultraviolet LED.

7. The catheter of claim 1, wherein the first ultraviolet LED delivers energy per illuminated tissue area in the range of from about 0 mJ/mm$^2$ to about 4.5 mJ/mm$^2$.

8. The catheter of claim 1, wherein the first ultraviolet LED delivers energy per illuminated tissue area in the range of from about 3 mJ/mm$^2$ to about 3.4 mJ/mm$^2$.

9. The catheter of claim 1, wherein the tissue is the endocardium, mid-myocardium, or epicardium of any of the chambers of the heart.

10. The catheter of claim 1, wherein the distal end has a rounded tip for contacting the tissue.

11. The catheter of claim 1, wherein the first ultraviolet LED has a different power than the second ultraviolet LED.

12. The catheter of claim 1, wherein the first ultraviolet LED to photobleach NADH in the tissue has a power of 500 mW.

13. The catheter of claim 1, wherein the second ultraviolet LED to illuminate the tissue for fluorescence imaging has a power of 1.5 mW.

14. A catheter to monitor enzyme activity in tissue comprising:
an ultraviolet illumination device disposed at a distal end of the catheter for exciting cellular, including mitochondrial, NADH of the tissue, wherein the ultraviolet illumination device comprises at least two ultraviolet light-emitting diodes (LEDs) including a first ultraviolet LED to photobleach NADH in the tissue and a second ultraviolet LED to thereafter illuminate the NADH in the tissue for fluorescence imaging;
a fiberscope disposed at the distal end of the catheter for detecting NADH fluorescence from the illuminated tissue at the distal end; and
a fluorescence light detector or camera at a proximal end of the catheter for creating a fluorescence measurement or image from detected NADH fluorescence captured by the fiberscope,
wherein the fluorescence measurement or image shows replenishment of fluorescent NADH after photobleaching, and this is indicative of cellular dehydrogenase enzyme kinetics within the tissue.

15. The catheter of claim 14, wherein the fluorescence light detector or camera includes a 460 nm band-pass filter to detect the NADH fluorescence from the tissue.

16. The catheter of claim 14, wherein the fluorescence camera is a CCD or EMCCD camera.

17. The catheter of claim 14, wherein the fiberscope comprises an optical imaging bundle.

18. The catheter of claim 14, wherein the first ultraviolet LED and second ultraviolet LED are connected by means of solid-state electronic components to a controller at the proximal end of the catheter, said controller configured to power and control the ultraviolet illumination device.

19. The catheter of claim 14, wherein the ultraviolet illumination device is comprised of one or more ends of a one or more optical energy delivering bundles said one or more optical energy delivering bundles traversing an interior of the catheter and connecting on the proximal end of the catheter with the first ultraviolet LED and the second ultraviolet LED.

20. The catheter of claim 14, wherein the first ultraviolet LED delivers energy per illuminated tissue area in the range of from about 0 mJ/mm$^2$ to about 4.5 mJ/mm$^2$.

21. The catheter of claim 14, wherein the first ultraviolet LED delivers energy per illuminated tissue area in the range of from about 3 mJ/mm$^2$ to about 3.4 mJ/mm$^2$.

22. The catheter of claim 14, wherein the tissue is the endocardium, mid-myocardium, or epicardium of any of the chambers of the heart.

23. The catheter of claim 14, wherein the distal end has a rounded tip for contacting the tissue.

24. A method for imaging a tissue comprising:
photobleaching NADH in the tissue, using a first light energy delivered by a first ultraviolet LED;
illuminating NADH in the tissue, using a second light energy delivered by a second ultraviolet LED; and
imaging fluorescence of illuminated NADH in the tissue to produce a recording of the imaged, illuminated tissue, the recording illustrating cellular dehydrogenase enzyme kinetics in the tissue.

25. The method of claim 24, wherein the step of photobleaching NADH in the tissue comprises temporarily reducing the fluorescence of mitochondrial NADH by at least 10% without harming the tissue.

26. The method of claim 24, wherein the step of illuminating NADH in the tissue is repeated at intervals to enable observation of the amount of NADH fluorescence over time while the NADH fluorescence recovers after the photobleaching step.

27. The method of claim 24, wherein the first light energy delivers energy per illuminated tissue area in the range of from about 0 mJ/mm$^2$ to about 4.5 mJ/mm$^2$.

28. The method of claim 24, wherein the first light energy delivers energy per illuminated tissue in the range of from about 3 mJ/mm$^2$ to about 3.4 mJ/mm$^2$.

29. The method of claim 24, wherein the second light energy is weaker than the first light energy.

30. The method of claim 24, comprising an additional step of calculating cellular dehydrogenase enzyme kinetics values for the tissue, wherein said calculating step is automatically performed by a computing system configured to receive and process the recordings of the imaged, illuminated tissue.

31. The method of claim 24, further comprising capturing light emitted from the illuminated tissue.

32. The method of claim 24, wherein the imaging of tissue is performed in real time.

33. The method of claim 24, wherein the acquisition of tissue fluorescence after tissue photobleaching forms the basis of a therapeutic procedure or diagnosis or monitoring of normal or pathologic conditions.

34. The method of claim 24, wherein the tissue is the endocardium, mid-myocardium, or epicardium of cardiac tissue.

* * * * *